(12) United States Patent
Feagler et al.

(10) Patent No.: US 12,399,050 B2
(45) Date of Patent: Aug. 26, 2025

(54) THERMAL MASS FLUID FLOW SENSOR

(71) Applicant: Becton, Dickinson and Company, Franklin Lakes, NJ (US)

(72) Inventors: Cole Emerson Feagler, Irvine, CA (US); Sakyasingh Tripathy, San Diego, CA (US); Brian Ray Hipszer, Irvine, CA (US); Feras Al Hatib, Irvine, CA (US); Hengchu Cao, Irvine, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 28 days.

(21) Appl. No.: 17/352,240

(22) Filed: Jun. 18, 2021

(65) Prior Publication Data
US 2021/0310840 A1  Oct. 7, 2021

Related U.S. Application Data

(63) Continuation of application No. PCT/US2019/065917, filed on Dec. 12, 2019.
(Continued)

(51) Int. Cl.
*G01F 1/688* (2006.01)
*G01F 1/684* (2006.01)

(52) U.S. Cl.
CPC ............ *G01F 1/688* (2013.01); *G01F 1/6845* (2013.01); *G01F 1/6847* (2013.01)

(58) Field of Classification Search
CPC ...... G01F 1/6845; G01F 1/6847; G01F 1/688; A61M 5/16886
See application file for complete search history.

(56) References Cited

U.S. PATENT DOCUMENTS 1,156,638 A * 10/1915 Simmons ................ G01F 1/684
                                                                73/204.25
2,583,561 A *  1/1952 General .................. G01F 1/696
                                                                73/204.17
(Continued)

FOREIGN PATENT DOCUMENTS

CN        103369748 A      10/2013

OTHER PUBLICATIONS

Alberta Health Services; "Central Zone Blood Component Administration Quick Reference Chart-Adult"; Jun. 2017; Ver. 1.1 (Year: 2017).*

(Continued)

*Primary Examiner* — Justin N Olamit
(74) *Attorney, Agent, or Firm* — Dority & Manning, P.A.

(57) ABSTRACT

Described herein are thermal mass flow sensors that combine calorimetric and anemometric (e.g., hot-wire) elements to provide a hybrid approach to determining flow rate of a liquid. The flow probes or flow sensors are configured to use a heater to apply heat to a thermally-conducting material in contact with the flowing liquid, to measure a temperature of the thermally-conducting material upstream of the heater and downstream or at the heater, to adjust power to the heater to achieve a targeted temperature difference, and to determine a flow rate based at least in part on the power supplied to the heater and the measured temperatures. This approach provides flow rate due at least in part to the fluid cooling the thermally-conductive material proportionate to flow rate with non-linear effects. This hybrid approach can provide accurate readings of flow rates of liquids delivered through an IV line to a patient.

30 Claims, 6 Drawing Sheets

Related U.S. Application Data

(60) Provisional application No. 62/782,597, filed on Dec. 20, 2018.

(56) References Cited

U.S. PATENT DOCUMENTS

| | | | |
|---|---|---|---|
| 4,384,578 A * | 5/1983 | Winkler | A61M 5/16886 |
| | | | 73/204.22 |
| 4,548,078 A * | 10/1985 | Bohrer | G01F 1/698 |
| | | | 73/204.22 |
| 4,651,564 A * | 3/1987 | Johnson | G01F 1/6845 |
| | | | 73/204.26 |
| 4,713,970 A | 12/1987 | Lambert | |
| 4,813,280 A | 3/1989 | Miller, Jr. et al. | |
| 5,339,687 A | 8/1994 | Gimson et al. | |
| 5,410,912 A | 5/1995 | Suzuki | |
| 6,318,171 B1 | 11/2001 | Suzuki | |
| 6,354,150 B1 | 3/2002 | Rudent et al. | |
| 6,361,206 B1 * | 3/2002 | Bonne | G01N 1/2247 |
| | | | 73/204.22 |
| 6,550,325 B1 * | 4/2003 | Inushima | G01F 15/006 |
| | | | 73/204.26 |
| 6,736,005 B2 | 5/2004 | McMillan et al. | |
| 6,883,370 B2 | 4/2005 | Vincze et al. | |
| 6,981,410 B2 * | 1/2006 | Seki | G01F 1/692 |
| | | | 73/204.26 |
| 7,107,835 B2 | 9/2006 | Korniyenko et al. | |
| 7,387,022 B1 | 6/2008 | Korniyenko et al. | |
| 7,788,047 B2 | 8/2010 | Schick et al. | |
| 7,895,888 B2 | 3/2011 | Hasebe | |
| 8,506,162 B2 | 8/2013 | Schick et al. | |
| 8,802,006 B2 | 8/2014 | Thomas et al. | |
| 8,887,477 B2 | 11/2014 | Falotico et al. | |
| 9,157,781 B2 * | 10/2015 | Sella | G01F 1/6965 |
| 9,186,457 B2 | 11/2015 | Lee | |
| 9,575,087 B2 | 2/2017 | Schick et al. | |
| 9,642,966 B2 | 5/2017 | Lee | |
| 9,696,191 B2 | 7/2017 | Pfau et al. | |
| 10,288,464 B2 * | 5/2019 | Harada | G01F 1/6888 |
| 10,598,529 B2 * | 3/2020 | Skarping | G01F 1/684 |
| 2001/0027684 A1 * | 10/2001 | Lotters | G01F 1/698 |
| | | | 73/204.27 |
| 2003/0130625 A1 | 7/2003 | Jacobson et al. | |
| 2003/0221483 A1 * | 12/2003 | McMillan | G01F 1/699 |
| | | | 73/204.21 |
| 2004/0173019 A1 | 9/2004 | McMillan et al. | |
| 2006/0048568 A1 | 3/2006 | Korniyenko et al. | |
| 2011/0009720 A1 * | 1/2011 | Kunjan | A61B 5/14532 |
| | | | 600/581 |
| 2011/0011372 A1 | 1/2011 | Sturgess et al. | |
| 2012/0116348 A1 | 5/2012 | Katoh et al. | |
| 2012/0186509 A1 * | 7/2012 | Milijasevic | A61M 5/16854 |
| | | | 116/266 |
| 2012/0291540 A1 | 11/2012 | Cooke et al. | |
| 2017/0115149 A1 | 4/2017 | Silpachai et al. | |
| 2018/0053547 A1 * | 2/2018 | Juillerat | A61L 2/081 |

OTHER PUBLICATIONS

Omega. "Thermal Mass Flow Working Principle, Theory and Design". Downloaded Dec. 8, 2023. <https://www.omega.com/en-us/resources/thermal-mass-flow-working-principle-theory-and-design>.

International Search Report and Written Opinion for Application PCT/US2019/065917, mailed Apr. 15, 2020, 13 pages.

International Preliminary Report on Patentability for Application PCT/US2019/065917, mailed Jun. 16, 2021, 9 pages.

* cited by examiner

THERMAL MASS FLUID FLOW SENSOR

CROSS-REFERENCE TO RELATED APPLICATIONS

This application is a continuation of International Patent Application No. PCT/US2019/065917, filed on Dec. 12, 2019, which claims the benefit of U.S. Provisional Application No. 62/782,597, filed Dec. 20, 2018 and entitled "Thermal Mass Fluid Flow Sensor," the disclosures of both of which are hereby incorporated by reference in their entireties.

BACKGROUND

Field

The present disclosure generally relates to a thermal mass fluid flow sensor for measuring fluid flow via thermal mass transport.

Description of Related Art

Fluid boluses, sometimes referred to as fluid challenges, can be used in the fluid management of patients. A principle behind using fluid challenges is that by giving a small amount of fluid in a short period of time (e.g., a fluid bolus), the clinician can assess whether the patient has a preload reserve that can be used to increase the stroke volume with further fluids. Continuous cardiac output can be used to monitor a patient's response to a fluid challenge. Therapy guided by determining patients' responses to fluid challenges can lead to reduced hospital stays and fewer post-operative complications. Flow probes can facilitate the tracking of fluids delivered to the patient and can make the overall fluid management of the patient easier and more manageable.

SUMMARY

According to a number of implementations, the present disclosure relates to a flow probe that includes a housing with walls forming a conduit to allow a liquid to flow therethrough. The flow probe also includes a thermally-conductive material secured to a portion of the walls so that the thermally-conductive material is in thermal contact with a liquid flowing through the conduit. The flow probe also includes a heating element in thermal contact with the thermally-conductive material so that the heating element is not exposed to the conduit. The flow probe also includes a proximal temperature sensor upstream of the heating element, the proximal temperature sensor in thermal contact with the thermally-conductive material so that the proximal temperature sensor is not exposed to the conduit. The flow probe also includes a distal temperature sensor downstream of the heating element, the distal temperature sensor in thermal contact with the thermally-conductive material so that the distal temperature sensor is not exposed to the conduit. The flow probe also includes a controller in communication with the heating element, the proximal temperature sensor, and the distal temperature sensor. The controller is configured to control the heating element to apply heat to the thermally-conductive material; determine an upstream temperature based at least in part on signals received from the proximal temperature sensor; determine a downstream temperature based at least in part on signals received from the distal temperature sensor; adjust a power to the heating element based at least in part on a temperature differential between the downstream temperature and the upstream temperature, the adjustment to the power being configured to achieve a targeted temperature differential; and determine a liquid flow rate based on the adjusted heater power and the targeted temperature differential.

In some embodiments, the flow probe further includes system electronics in communication with the proximal and distal temperature sensors, the controller, and the heating element. In further embodiments, the system electronics includes large-scale electronics configured to withstand electron beam or gamma-ray sterilization. In further embodiments, the system electronics are not semi-conductor based. In yet further embodiments, the system electronics include discrete electronic components and MEMS-based fabrication techniques.

In some embodiments, the flow probe is shuntless. In some embodiments, the housing further includes a conformal coating of waterproof, biocompatible material on an inner side of the thermally-conductive film. In some embodiments, the flow probe includes luer lock connectors on a proximal end and a distal end of the housing. In some embodiments, the flow probe is configured for use in an intravenous line.

In some embodiments, the proximal temperature sensor is positioned between 25 mm and 50 mm from a proximal end of the conduit. In some embodiments, the distal temperature sensor is positioned less than or equal to 5 mm from a distal end of the heating element. In some embodiments, the proximal temperature sensor is a thin-film thermocouple. In some embodiments, the proximal temperature sensor is a thermistor. In some embodiments, the heating element is a thin-film heating element. In some embodiments, the flow probe is configured for use with liquids in a temperature range greater than or equal to 5 C and less than or equal to 50 C. In some embodiments, the flow probe is configured for use with liquids with flow rates in a range greater than or equal to 0 mL/min and less than or equal to 180 mL/min. In some embodiments, the flow probe is configured to be responsive to changes in flow rate in less than 1 second.

In some embodiments, the controller implements a proportional-integral-derivative control scheme to control the heating element. In some embodiments, the distal temperature sensor is integrated with the heating element. In some embodiments, the controller determines liquid flow rate using a lookup table that associates heater power to flow rate.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION OF SOME EMBODIMENTS

Figure 1:
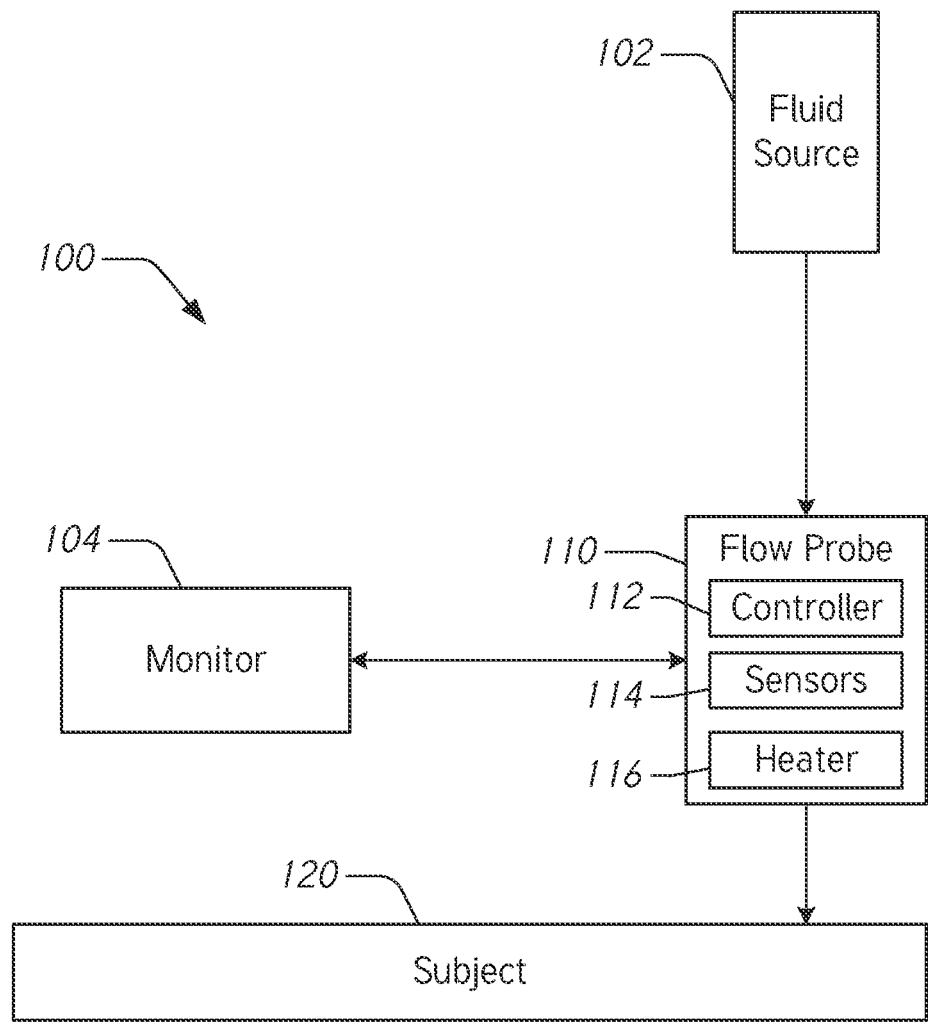
FIG. 1 illustrates an example embodiment of a subject monitoring system that includes a flow probe that senses a liquid flow rate (e.g., volume flow or mass flow) delivered to a subject.

The headings provided herein, if any, are for convenience only and do not necessarily affect the scope or meaning of the claimed invention.

Overview

Flow probes can be used to measure the fluid flow rate from a fluid source, like an IV bag, to a patient. A flow probe can be in a number of different configurations with respect to the fluid source such as, for example, a flow probe can be in line between the fluid source and the patient meaning that the flow of fluids passes through the flow probe, a flow probe can be attached to the conduit carrying the fluid, or a flow probe can be positioned (at least partially) within the conduit carrying the fluid. Flow probes in these configurations are different from systems that measure fluid flow or fluid delivery using other means such as by monitoring the weight of the fluid in the fluid source, measuring the level of fluid in the fluid source, measuring fluid at the patient end (e.g., fluid suctioned into a collection container), tracking movement of a piston or similar component in a pump, and the like. Flow probes can provide instantaneous measurements of fluid flow rate by measuring fluid flow in the conduit. Measurements from a flow probe can be used to track fluid boluses to aid in the fluid management of the patient as well as track maintenance fluid administrations, where maintenance fluids can be fluids that are continuously administered at a relatively slow flow rate over a long period of time.

A thermal mass flow probe is a particular species of a flow probe. Thermal mass flow probes or sensors typically determine a flow rate of a fluid or liquid by measuring thermal characteristics of the fluid and sensor. The thermal characteristics, such as temperature and heat, are related to the flow rate of the fluid. Thus, by measuring a temperature profile of a flowing fluid or tracking an amount of heat applied to a heater, a flow probe can determine an estimate of the fluid flow rate.

One class of thermal mass flow probe is a calorimetric flow probe. This class of flow probe is based on two temperature sensors in close contact with the fluid but thermally insulated from each other. A heater is used near the downstream sensor and is constantly heated. The cooling effect of the flowing fluid is used to determine the flowrate. In a stationary (no flow) fluid condition there is a constant temperature difference between the two temperature sensors. When the fluid flow increases, heat energy is drawn from the heated sensor and the temperature difference between the sensors are reduced. The reduction is proportional to the flow rate of the fluid. Thus, calorimetric systems measure the asymmetry of a temperature profile modulated by the fluid flow by using two different heat sensors surrounding a heating element.

Another class of thermal mass flow probe is a hot-wire or anemometric flow probe. This class of flow probe measures the effect of a flowing fluid on a resistive element that is also used as a heat sensor. Certain implementations of a hot-wire flow probe include an electrically heated, fine-wire element. When placed in a moving fluid, the wire cools and the rate of cooling corresponds to the mass flow rate. The flow probe typically operates in one of two modes: a constant power mode or a constant temperature mode. In the constant power mode, the flow probe applies a constant heater power and measures the change in resistance to the heating element to determine the corresponding cooling flow rate. In the constant temperature mode, the flow probe measures the change in heating power required to maintain a constant heater temperature. The constant-temperature flow probe maintains a constant temperature differential between a heated sensor and a reference sensor. The amount of power required to maintain the differential is measured as an indication of the mass flow rate.

However, there is a need for a thermal mass flow probe tailored for use in measuring liquid delivered through an intravenous line (IV) to a patient. Accordingly, described herein are thermal mass flow probes that combine calorimetric and anemometric (e.g., hot-wire) elements to provide a hybrid approach to determining flow rate of a liquid. The disclosed devices and methods are configured to use a heater to apply heat to a metal foil in contact with the flowing liquid, to measure a temperature of the incoming liquid, to measure a temperature of the metal foil at the heater, to adjust power to the heater to achieve a targeted temperature difference between the measured temperatures, and to determine a flow rate based at least in part on the power supplied to the heater and the measured temperatures. This hybrid approach provides flow rate due at least in part to the liquid cooling the metal foil proportionate to flow rate with non-linear effects. By combining these measurement techniques, the disclosed devices and methods advantageously provide accurate readings of flow rates of liquids delivered through an IV to a patient. This approach can advantageously provide a high-frequency response with a relatively low level of electronic noise, and relatively low power.

The hybrid flow probes and methods described herein combine calorimetric methods with anemometric methods. The calorimetric aspect of the described devices and methods measures the asymmetry of the temperature profile caused by fluid flow using two temperature sensors surrounding a heating element. The anemometric aspect of the described devices and methods measures the change in heating power required to maintain a targeted heater temperature, or, more specifically, a targeted temperature difference between the temperature sensors and the heater.

Advantageously, the described flow probes use a thin-film heater in conjunction with a thermally-conducting material that is in thermal contact with a liquid that flows through a conduit of the flow probe. In some embodiments, the thermally-conducting material can be in physical contact as well as in thermal contact with the liquid, such as when the thermally-conducting material lines a portion of an interior portion of the conduit. In some embodiments, the thermally-conducting material is not in direct physical contact with the liquid but is still in thermal contact with it. For example, the thermally-conducting material can be on an outer portion of the wall forming the conduit, at least partially embedded in the wall, or covered with a layer of material (e.g., a coating) that inhibits the thermally-conducting material from being in physical contact with the liquid but which still allows the material to be in thermal contact with it. Some implementations of the disclosed flow probes thus do not directly heat the liquid, which would require a relatively large amount of energy and/or potentially damage the liquid, rather these flow probes heat the thermally-conducting material. In some embodiments, the temperature sensors are configured to measure the temperature of the thermally-conducting material rather than the liquid. Advantageously, these disclosed flow probes provide improved sensitivity relative to flow probes that directly measure the temperature of the liquid. In addition, by physically isolating the sensors and heater from the liquid, there is no need to waterproof these and related components, resulting in more options being available for components for the flow probe.

In certain implementations, the disclosed flow probes are configured to maintain a targeted temperature differential between heated and unheated probes by varying heater power over time. The heater power can be varied continuously, periodically, or intermittently. The flow probes can include an online or integrated controller that is configured to dynamically adjust the power provided to the heater element to maintain the targeted temperature differential. For example, the controller can use proportional-integral-derivative (PID) control algorithms to dynamically adjust the power. The flow rate can be determined based on the power supplied to the heater. The controller can be configured to account for non-linear effects in such a system to correlate the amount of power supplied to liquid flow rates.

In some embodiments, the disclosed devices and methods include a flow probe with a control system for measuring liquid flow via thermal mass transport. The control system can be implemented directly in the flow probe using dedicated hardware and/or software installed on an integrated control unit. Liquid flow rate is measured by providing a known quantity of heat to the system (e.g., the sensor and liquid moving through the sensor) via a heating unit, then measuring the amount of heat carried away from the sensor by the moving liquid. For any given liquid, an increase in flow rate results in heat being drawn away from the heater at a higher rate. In various implementations, an online (e.g., real-time) controller scales the amount of heat delivered in response to changes in the flow rate. This can improve sensitivity and reduce or prevent overheating of the sensors and liquid.

In some embodiments, the disclosed flow probes include one or more of the following features in any suitable combination: (1) the device is not a semiconductor-based product (e.g., not a CMOS product), (2) the device is shuntless (e.g., the device includes a single, continuous passage for the entire volume of liquid), (3) the device includes a thin film of thermally-conductive material in thermal contact with the liquid stream and measures the temperature of the material rather than directly measuring the temperature of the liquid, (4) the device is designed to withstand electron beam or gamma-ray sterilization by using discrete or large-scale electronic components, (5) the device uses an integrated controller to regulate heater power, and (6) the device is specifically designed for tracking fluid flow in an IV line.

First, some embodiments of the disclosed flow probes are not semiconductor-based (e.g., CMOS). Rather, the disclosed flow probes are manufactured using discrete electronic components (e.g., thermistors, polyimide, wire heater mats, etc.) and/or MEMS-based fabrication techniques (excluding silicon-based techniques).

Second, some embodiments of the disclosed flow probes are shuntless (e.g., there is no secondary passageway or lumen for a portion of the liquid to flow through for measurement purposes). The entire volume of liquid to be measured flows through a single, continuous passage for the length of the flow probe. This provides some advantages, such as simplifying manufacturability, eliminating complex calculations and calibrations to relate the proportion of liquid passing through the shunt as compared to a main flow path, and the like.

Third, rather than directly measuring the temperature of the moving liquid (which can damage sensitive measurement electronics or necessitate complex and costly protective measures), some embodiments of the disclosed flow probes include a thin film of thermally-conductive material in thermal contact with the liquid flowing through the sensor. The probes work by measuring the temperature of the film which is then correlated to the temperature of the liquid. In some implementations, a conformal coating of waterproof, biocompatible material may be applied to the inside of the flow probe to further isolate the electronics and/or the thermally-conducting material of the flow probe.

Fourth, some embodiments of the disclosed flow probes may be capable of better withstanding electron beam or gamma-ray sterilization than existing thermal mass flow meters, especially those implemented on semiconductor substrates. Radiation-based sterilization of medical equipment is faster than traditional chemical-based sterilization. However, these sterilization techniques frequently cause damage to electronics. By fabricating the flow probe using discrete components and/or slightly larger-scale electronic components, the sensor can survive radioactive sterilization. The disclosed flow probes can also include shielding of the electronics to reduce damage caused by e-beam sterilization.

Fifth, some embodiments of the disclosed flow probes use an online controller to regulate heater power. The online controller is included on the flow probe and is configured to provide real-time control of power to a heater. Regulation of the heater power is correlated to flow rates.

Sixth, some embodiments of the disclosed flow probes are designed for the precise application of tracking fluid flow in an IV line. The custom design for such an application includes the scale of the fluid probe, the use of biocompatible materials, a flexible design allowing for direct integration with an IV extension set, the choice of thermal mass flow sensing with particular consideration given to the ability to measure flow over a relatively wide range of flow rates, and/or limitations on heating the liquid in the IV line. For example, the disclosed flow probes are configured to apply heat to a thermally-conducting material rather than to the liquid directly to limit or prevent over-heating and damaging the liquid. This also advantageously reduces energy requirements for the disclosed flow probes.

The following description illustrate some example embodiments in detail. Those of skill in the art will recognize that there are numerous variations and modifications of the present disclosure that are encompassed by its scope. Accordingly, the description of certain embodiments should not be deemed to limit the scope of the disclosure. Moreover, the disclosed flow probes can be used in any suitable fluid monitoring system in addition to the fluid monitoring systems described herein.

Subject Monitoring System with Flow Probe

FIG. 1 illustrates an example embodiment of a subject monitoring system 100 that includes a flow probe 110 that senses a liquid flow rate (e.g., volume flow or mass flow) delivered to a subject or patient 120. Based at least in part on the sensed flow rate, the flow probe 110 provides flow-related data that the system 100 can use to derive a volume of fluid being delivered. The fluid can be delivered from a fluid source 102 that can include an IV bag, another in-line port, or a combination of the two. The system 100 can include a monitor 104 that can receive the flow-related data from the flow probe 110 and can display this information. In some embodiments, the monitor 104 can be configured to determine when a fluid bolus is being delivered based on flow rate data received from the flow probe 110 and can differentiate this from fluid maintenance flow rates. In some embodiments, the monitor 104 and/or the flow probe 110 can be configured to display the determined flow rate. A clinician can use this information to gain an understanding of the volume of fluid/mass the subject 120 has received. The system 100 finds particular applicability in determining and tracking the amount of liquid delivered to the subject 120.

The flow probe 110 (which may also be referred to as a "mass flow sensor" or a "flow rate sensor") is configured to be in line between the fluid source 102 and the subject 120. This means that the flow of liquid passes through the flow probe 110, that the flow probe 110 is attached to the conduit carrying the fluid, or that the flow probe 110 is positioned (at least partially) within the conduit carrying the liquid. Such systems can be differentiated from systems that measure fluid flow or fluid delivery using other means such as by weight of the fluid in the fluid source, the level of fluid in the fluid source, a measure of fluid at the patient end (e.g., fluid suctioned into a collection container), movement of a piston or similar component in a pump, and the like. In addition, the flow probe 110 can be configured to determine a flow rate using a combination of calorimetric and anemometric techniques (e.g., combining temperature measurements with heater power data).

The flow probe 110 includes an integrated controller 112, a plurality of temperature sensors 114, and a heater 116. The flow probe 110 is configured to apply heat to the liquid flowing through the flow probe by providing power to the heater which in turn heats a thermally-conductive material in contact with the liquid. At least one of the temperature sensors 114 measures the temperature of the thermally-conductive material upstream of the heater 116 and at least one other sensor of the temperature sensors 114 measures the temperature of the thermally-conductive material at the heater 116 and/or downstream of the heater 116. The controller receives the temperature measurements from the sensors 114 and determines the difference between the upstream temperature and the temperature at the heater 116. The controller 112 determines an adjustment to the power to deliver to the heater 116 to achieve a targeted temperature difference based at least in part on the determined temperature difference. The controller 112 dynamically updates the power delivered to the heater 116 to achieve the targeted temperature based on updated temperature measurements received from the sensors 114.

In some embodiments, the controller 112 can be part of the monitor 104 or at least a portion of the controller can be part of the monitor 104. For example, the monitor 104 can be configured to determine or receive an indication of the power provided to the heater 116 and the temperatures measured by the sensors 114. The monitor 104 can be configured to display the received parameters and/or to display additional data determined based on the received parameters.

The flow probe data can be used to present flow-related data on the monitor 104 or another display via numerical, textual, or pictorial information. This can be displayed or presented in addition to hemodynamic data. The information can include a dynamic mass flow rate and/or a mass flow rate history. The information can also include one or more recommendations as to fluid administration protocols. In some embodiments, the monitor 104 provides a user interface to allow a user to adjust characteristics of the flow probe 110. In some embodiments, the monitor 104 provides a user interface that provides diagnostic data, calibration data, status information, or other information related to the flow probe 110.

Embodiments of the flow probe 110 can provide dynamic, continuous, intermittent, or on-demand flow rate data in the form of analog or digital signals for use by the monitor 104 or a healthcare provider. The flow probe 110 can be cooperatively engaged with a flow controller and controlled by an algorithm. For example, the flow probe 110 and a flow controller can be used in an open-loop or closed-loop feedback system to control liquid flow (e.g., from the fluid source 102) based at least in part on measured flow-related data.

In some embodiments, the system 100 includes one or more physiological sensors that provide physiological data to the monitor 104. The physiological sensors can include a hemodynamic sensor, for example. The hemodynamic sensor can be the FLOTRAC® sensor, in certain implementations. The physiological sensor can be configured to provide information capable of being transformed into one or more forms of heart output data. In some embodiments, an oximetry device can be used as part of the physiological sensor. In certain embodiments, the oximetry device can be a finger cuff device that is integrated with the system 100, system electronics, and/or the monitor 104. The system 100 can utilize the physiological data in an algorithm to determine how the subject 120 responds to administered fluid volumes. Based on the correlated sensed data from the flow probe 110 and the data from the physiological sensor, the algorithm can determine the response of the subject 120, provide information (e.g., a recommendation) to the clinician regarding subsequent bolus administration, and/or control the amount and rate of volume of fluid delivered to the subject 120, e.g., using a flow controller.

Example Embodiments of Flow Probes

Figure 2:
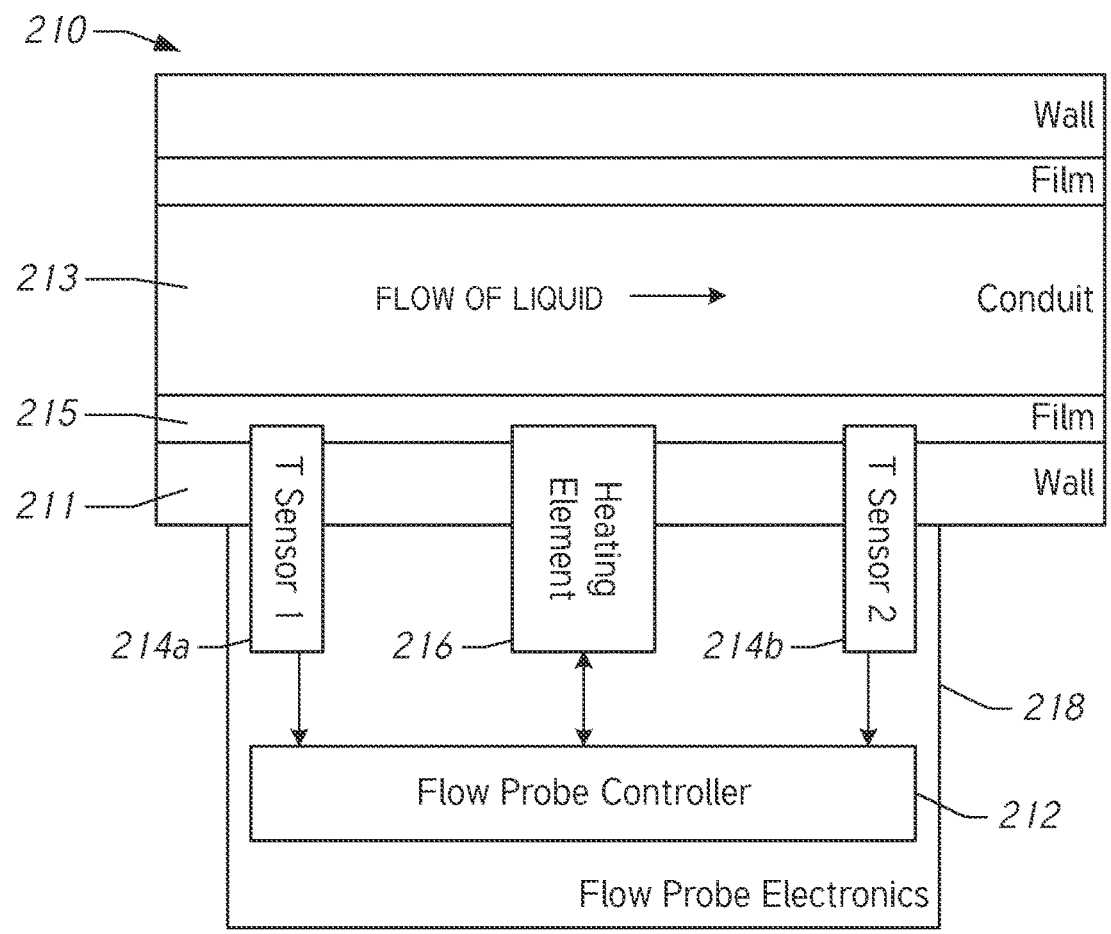
FIG. 2 illustrates a block diagram of an example flow probe that is configured to determine liquid flow rates based on a hybrid measurement approach.

FIG. 2 illustrates a block diagram of an example flow probe 210 that is configured to determine liquid flow rates based on a hybrid measurement approach. The flow probe includes a housing with walls 211 that form a conduit 213 through the flow probe 210 to allow liquid to flow therethrough. The flow probe 210 includes thermally-conductive material 215, such as a metal foil or film, attached to the walls 211 along a portion of the walls 211.

The flow probe 210 includes flow probe electronics 218 that include a flow probe controller 212, temperature sensors 214a, 214b, and a heating element 216. The flow probe electronics 218 can also include a power supply, such as a battery, wireless and/or wired communication systems and ports, one or more data stores to store measurement data, calibration data, algorithms, computer-executable instructions, and the like.

The flow probe 210 is configured to measure fluid flow via thermal mass transport. The flow probe 210 includes a shuntless design wherein the entire volume of fluid to be measured flows through the conduit 213, which is a single, continuous passage. The flow probe 210 includes a film 215 of thermally-conductive material. The flow probe 210 is configured to measure the temperature of the film 215 rather than directly measuring the temperature of the liquid in the conduit 213. The controller 212 regulates the heater power to the heating element 216. Based on the heater power delivered and the temperatures measured, the flow rate can be determined by the flow probe controller 212.

In some embodiments, the flow probe 210 is not a semiconductor-based product (e.g., not a complementary metal oxide semiconductor or CMOS). That is, the flow probe electronics 218 are not implemented on a substrate as with typical printed circuit boards. The flow probe electronics 218 can be manufactured using discrete electronic components (e.g., thermistors, polyimide, wire heater mats, etc.) and/or MEMS-based fabrication techniques (excluding silicon-based techniques). The flow probe electronics 218 use larger-sized components. This is done, in part, to increase the robustness of the flow probe 210 to sterilization techniques that employ radiation that can damage or destroy semi-conductor-based electronics boards. For example, the flow probe electronics 218 can include larger-scale electronics to withstand electron beam or gamma-ray sterilization. The flow probe electronics 218 can use slightly larger-scale electronic components so that the flow probe 210 survives radioactive sterilization. The disclosed flow probes can also include shielding of the electronics to reduce damage caused by e-beam sterilization.

The flow probe 210 can be configured specifically for tracking liquid flow through an intravenous line. For example, the walls 211 of the flow probe 210 can include luer lock connectors on proximal and distal ends to facilitate insertion of the flow probe 210 in an IV line. Other connectors can be included on the proximal and/or distal ends of the housing to create a continuous conduit from an insertion line to an out-flow line.

The flow probe 210 is configured to apply heat to the film 215 (e.g., a metal foil) using the heating element 216. The flowing liquid cools the film 215 in a way that is related to the flow rate where the relationship includes non-linear effects. The flow probe 210 measures the temperature of the incoming liquid with a proximal or upstream temperature sensor 214a and measures the temperature of the heating element 216 or the film 215 downstream of the heating element using a distal or downstream temperature sensor 214b. The controller 212 uses an algorithm based on the measured temperatures to dynamically vary power to the heating element 216 to maintain a constant or targeted temperature difference between the incoming liquid and the film 215. In some embodiments, the controller 212 is a proportional-integral-derivative controller (or PID). The input power is correlated to flow rate so that the controller 212 can determine changes in the flow rate based on the adjustments to the heater power.

The flow probe 210 can be configured to adjust or to control the electronic system (e.g., the temperature sensors 214a, 214b and heating element 216) to tune PID control parameters. The flow probe 210 can be configured to tailor the targeted temperature difference for suitable or desirable results in the range of flow rates and liquid temperatures expected in an IV line. For example, the flow probe 210 can be tailored or optimized to operate in a temperature range of at least about 5° C. and/or less than or equal to about 50° C., at least about 15° C. and/or less than or equal to about 45° C., at least about 20° C. and/or less than or equal to about 40° C., or at least about 22° C. and/or less than or equal to about 38° C. As another example, the flow probe 210 can be tailored or optimized to operate in a flow rate range of at least about 0 mL/min (e.g., no flow) and/or less than or equal to about 180 mL/min, at least about 5 mL/min and/or less than or equal to about 170 mL/min, at least about 10 mL/min and/or less than or equal to about 100 mL/min, or at least about 15 mL/min and/or less than or equal to about 70 mL/min. The flow probe 210 can be configured to have a sensor response time with a 90% response within at least about 15 seconds, within at least about 10 seconds, within at least about 7 seconds, within at least about 5 seconds, within at least about 2 seconds, or within at least about 1 second.

For the characterization of the heating element 216, the flow probe controller 212 can be configured to relate temperature sensor measurements (e.g., thermistor response signals) to input power provided to the heating element 216. The controller 212 can be configured to account for linear and non-linear behavior as well as time lag. An advantageous aspect of this design is that there is no need for a full mathematical model of the flow probe. The heating element 216 can include wound resistive wire (e.g., Constantan 0.025"), a thin-film heater, or the like. In some embodiments, induction heating is avoided due at least in part to the high power requirements, making it undesirable in a low-temperature heating application that is the case for measuring liquid flow rates in an IV line.

In some embodiments, the flow probe electronics 218 include a precision power regulator. For example, a 14-bit digital-to-analog converter (DAC) can be used to provide sub-millivolt resolution over a range covering about 15 V. Other DACs (e.g., 12-bit DAC, 16-bit DAC) may be used to provide different voltage resolutions over preferred or desired voltage ranges. The power regulator can be on-board the probe with continuously controllable and precision power regulation to the heating element 216. In some embodiments, the power regulator can have a relatively fast response time. For example, the response time can be less than about 500 µs, less than about 1 ms, less than about 10 ms, less than about 25 ms, less than about 50 ms, or less than about 100 ms. In certain embodiments, the power regulator can include a DAC in conjunction with pulse-width-modulation (PWM) to emulate a power regulator with a relatively fast response time (e.g., less than about 500 µs, less than about 1 ms, less than about 10 ms, less than about 25 ms, less than about 50 ms, or less than about 100 ms). The response time of the power regulator can be configured to ensure that the sensor provides a targeted response time of less than about 15 s, less than about 10 s, less than about 7 s, less than about 5 s, less than about 2 s, or less than about 1 s.

In some embodiments, one or more of the temperature sensors 214a, 214b can be integrated into the heating element 216. For example, a heating element temperature sensor combination can be provided using micro-electromechanical system (MEMS) technology.

In some embodiments, the temperature sensors 214a, 214b can be thermistors. The flow probe controller 212 can be configured to account for calibration temperature when characterizing the flow probe system 210.

The temperature sensors 214a, 214b can be configured to be in contact with the film 215 rather than the liquid in the conduit 213. Similarly, the heating element 216 is configured to directly heat the film 215 rather than the liquid in the conduit 213. In some embodiments, the temperature sensors 214a, 214b and/or the heating element 216 is secured to the film 215 or foil using thermally-conductive bonding material to ensure contact with the film 215 and accurate temperature measurements. In certain implementations, the temperature sensors 214a, 214b can be thermistors encapsulated in a glass bead that are bonded to the metal foil or film 215 using, for example, a thermal paste and/or an adhesive resin. Flexible circuitry thermistors, thermocouples, thin-film thermocouples, or resistance temperature detectors (RTDs) may also be used for one or more of the temperature sensors 214a, 214b.

In some embodiments, the heating element 216 includes bi-wound lead wires to reduce or eliminate self-generated electromagnetic interference. The heating element 216 may also be a wrapped metal core with electrically-insulating, thermally-conductive pads. In some embodiments, the heating element 216 is a thin metal element or thin film heater that is thermally coupled to the film or metal foil 215. The flow probe 210 can be configured to measure the temperature of the heating element 216 away from the heating zone (e.g., using the downstream temperature sensor 214b or a dedicated temperature sensor with the heating element 216).

Because the heating element 216 and the temperature sensors 214a, 214b are not in physical contact with the liquid, this advantageously improves sensitivity, reduces energy input, reduces the amount of heating of the IV fluid, improves biocompatibility, and eliminates the need to waterproof thermistors. To improve performance of the flow probe 210, the positioning of the thermistors can be tuned so that the upstream temperature sensor 214a measures temperature in a laminar flow region of the conduit 213. Similarly, the downstream temperature sensor 214b can be positioned distally of the heating element so that it is away from the heating zone but near the heating element 216 to accurately measure its temperature. In addition, the flow probe 210 can include a characterization of the transfer of heat to the liquid as a function of power input to the heating element 216. As a result, the flow probe 210 can be configured to maintain a targeted or constant temperature differential between the heated and unheated probes, or the downstream temperature sensor 214b and the upstream temperature sensor 214a, by continuously, intermittently, or periodically varying heater power. The flow rate can be inferred from the power provided to the heating element 216 to maintain this targeted temperature difference.

Figure 3:
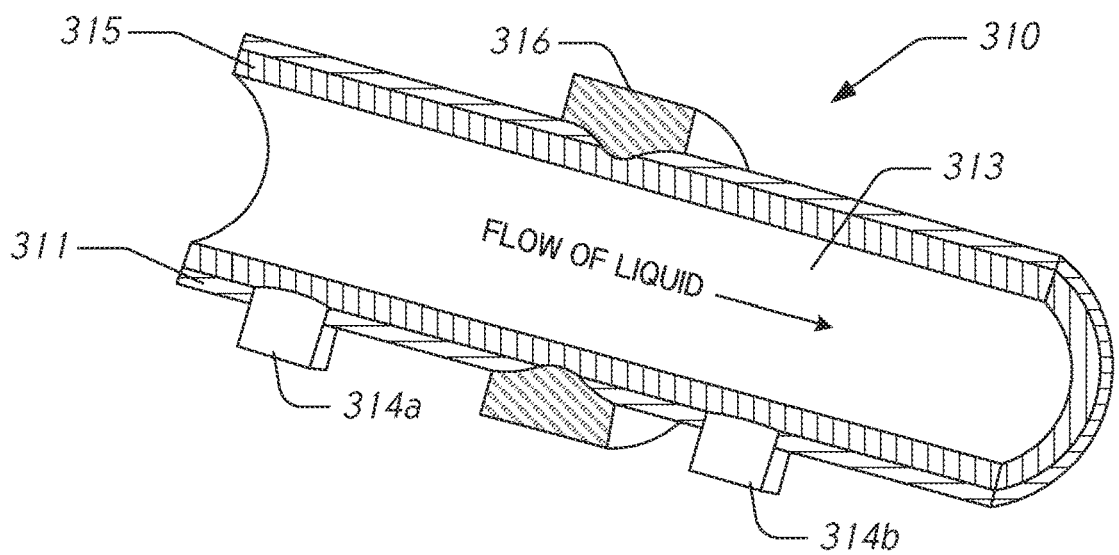
FIG. 3 illustrates an embodiment of the flow probe of FIG. 2.

FIG. 3 illustrates an example embodiment of a flow probe 310 that is similar to the flow probe 210 described herein with reference to FIG. 2. The flow probe 310 includes a housing that has walls 311 that form a conduit 313 therethrough for a liquid to flow. The flow probe 310 includes a metal foil 315 secured to the walls 311 for at least a portion of the path through the conduit 313. The flow probe 310 includes a heating element 316 that is configured to provide heat to the metal foil 315. The flow probe 310 also includes a proximal thermistor 314a and a distal thermistor 314b on either side of the heating element 316 and in contact with the metal foil 315 outside of the conduit 313. In this way, the thermistors 314a, 314b and the heating element 316 are not in contact with the liquid flowing through the conduit 313. The proximal thermistor 314a is configured to measure a temperature of the metal foil 315 upstream of the heating element 316. This temperature measurement is indicative of the temperature of the liquid in the conduit 313. The distal thermistor 314b is configured to measure a temperature of the metal foil 315 downstream of the heating element 316. This temperature measurement is indicative of the temperature of the heating element 316 and/or the metal foil 315 downstream of the heating element 316. Although not illustrated here, it should be understood that the flow probe 310 includes other electronics, similar to the flow probe electronics 218 of FIG. 2, that are integrated with the flow probe 310 and can be housed within the housing of the flow probe 310.

The flow probe 310 is designed so that there is laminar flow at the proximal thermistor 314a. For example, the proximal thermistor 314a can be placed at least 25 mm and/or less than or equal to about 50 mm from a proximal end of the conduit 313. As another example, the proximal thermistor 314a can be placed less than or equal to about 30 mm from a proximal end of the conduit 313, less than or equal to about 35 mm from a proximal end of the conduit 313, less than or equal to about 40 mm from a proximal end of the conduit 313, less than or equal to about 45 mm from a proximal end of the conduit 313, less than or equal to about 50 mm from a proximal end of the conduit 313, or less than or equal to about 55 mm from a proximal end of the conduit 313. These placements can ensure that laminar flow has developed in the conduit 313 even where the flow rate is relatively high (e.g., greater than or equal to about 180 mL/min). Similarly, the distal thermistor 314b is positioned downstream of the heating element 316 a tailored distance to capture an accurate measurement of the temperature of the heated liquid before it has cooled too much. This may be useful because flow rate differences are more distinguishable the closer to the heating element 316 the temperature measurement is acquired. The farther from the heating element 316 the temperature measurement is acquired, the smaller the differences in temperatures are for differing flow rates. In some embodiments, the distal thermistor 314b can be placed at least 2 mm from the distal end of the heating element 316 and/or less than or equal to about 5 mm from the distal end of the heating element 316, at least 1 mm from the distal end of the heating element 316 and/or less than or equal to about 8 mm from the distal end of the heating element 316, or less than or equal to about 10 mm from the distal end of the heating element 316. The precise placement may be tailored or optimized to provide a beneficial balance between stability and sensitivity. Thus, the distance from the end of the heating element 316 to the distal thermistor 314b can be as small as operably feasible to reduce or minimize heater power requirements due at least in part to the temperature fall off with distance from the heating element 316.

The heating element 316 can extend laterally to increase the distance along which the metal foil 315, and therefore the liquid in the conduit 313, is heated. A longer or larger heating element 316 facilitates quicker heat transfer to the metal foil 315 and the liquid. Larger or longer heaters also may cause heat to be transferred further away from the boundary at the wall 311 resulting in liquid further from the wall being heated.

Figure 4:
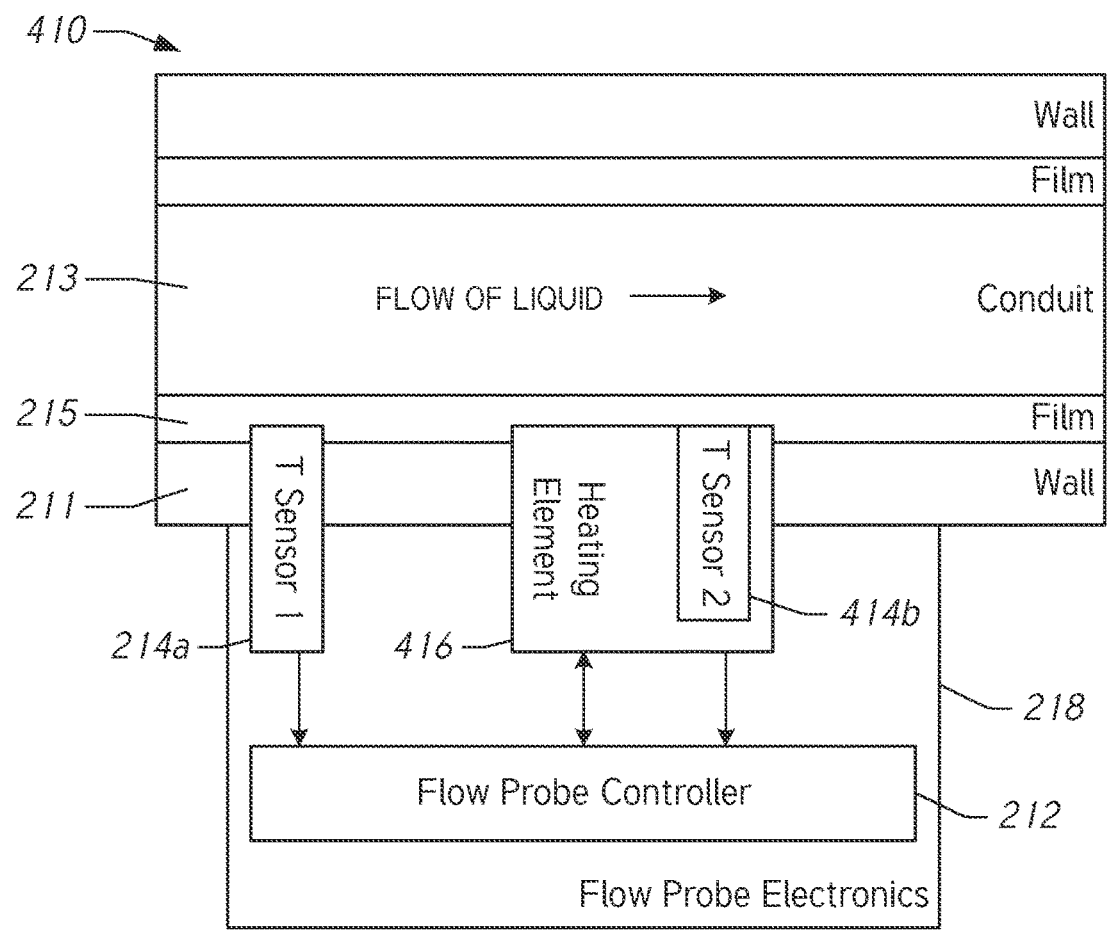
FIG. 4 illustrates a block diagram of another example flow probe that is configured to determine liquid flow rates based on a hybrid measurement approach.

FIG. 4 illustrates a block diagram of another example flow probe 410 that integrates a downstream temperature sensor 414b with the heating element 416. In other respects, the flow probe 410 is similar to the flow probe 210 described herein with reference to FIG. 2. The flow probe 410 may be able to provide a more accurate measurement of the film 215 at the heating element 416, which may improve the accuracy and stability of flow rate calculations. In addition, this design enables other temperature sensor technologies to be used such as thin-film thermocouples that can be used with thin-film heating elements. Elements that are common between the flow probes 210 and 410 retain their respective callouts and a description of these common components will not be repeated here for the sake of clarity and conciseness.

Figure 5:
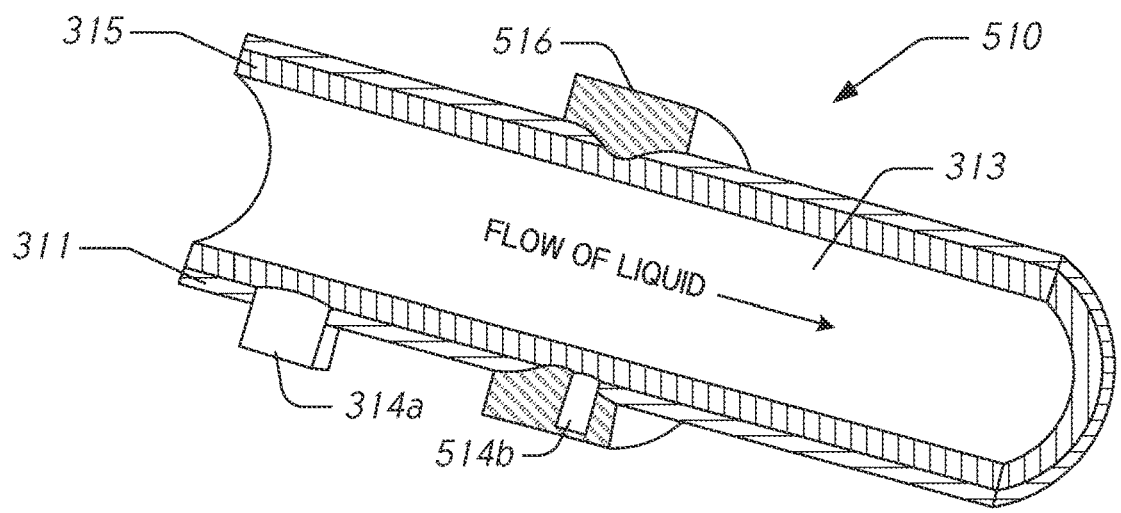
FIG. 5 illustrates an embodiment of the flow probe of FIG. 4.

FIG. 5 illustrates another example flow probe 510, where the flow probe 510 is an embodiment of the flow probe 410 described herein with reference to FIG. 4. The flow probe 510 is also similar to the flow probe 310 described herein with reference to FIG. 3 with a difference being that the distal thermistor 514b is integrated with, or bonded to, the heating element 516. As with the flow probe 410, this design enables other temperature sensor technologies to be used such as thin-film thermocouples that can be used with thin-film heating elements. Elements that are common between the flow probes 310 and 510 retain their respective callouts and a description of these common components will not be repeated here for the sake of clarity and conciseness.

Figure 6:
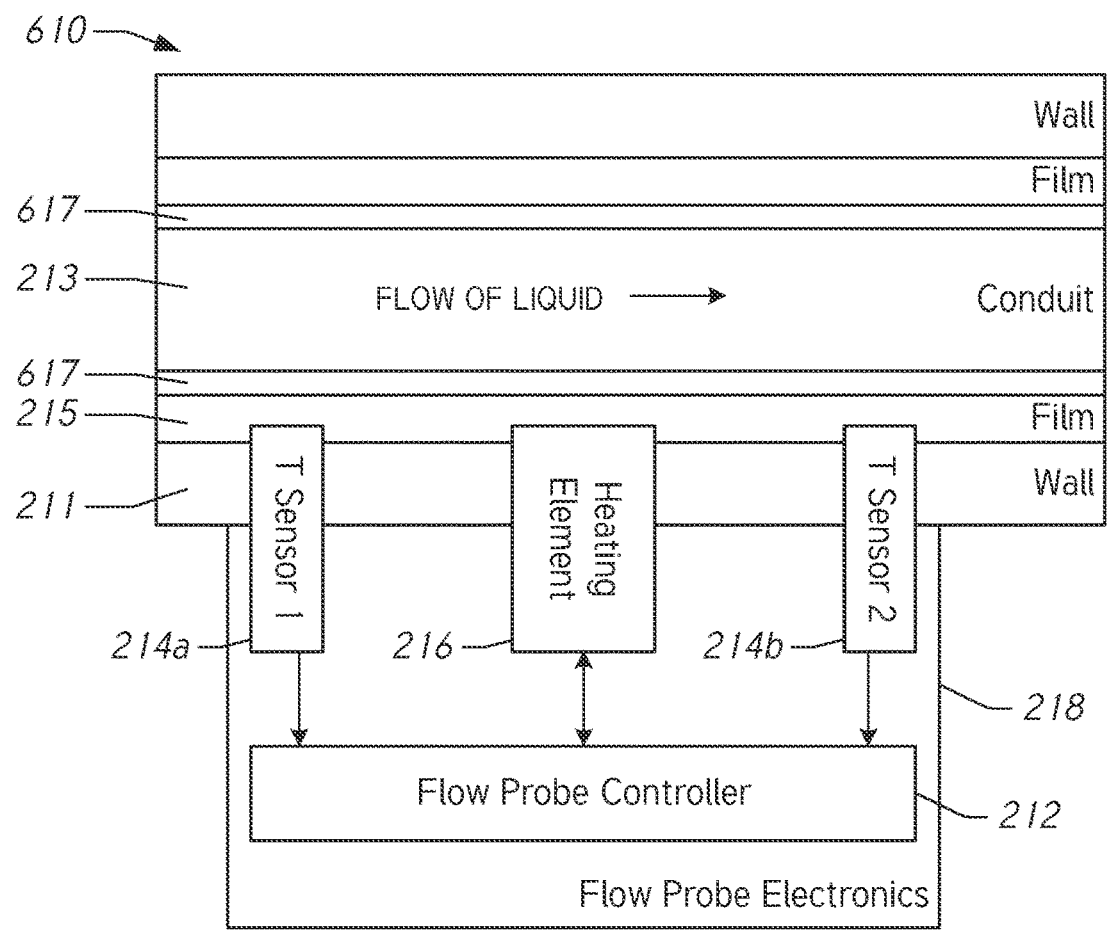
FIG. 6 illustrates a block diagram of another example flow probe that includes an inner layer between a thermally-conductive material and liquid flowing through a conduit.

FIG. 6 illustrates a block diagram of another example flow probe 610 that includes an inner layer 617 between the thermally-conducting film 215 and the conduit 213. In other respects, the flow probe 610 is similar to the flow probe 210 described herein with reference to FIG. 2. The inner layer 617 can be a coating, a portion of the wall 211, or other similar material or feature that prevents physical contact between a liquid flowing through the conduit 213 and the film 215 but that still allows thermal contact between the liquid and the film 215. Elements that are common between the flow probes 210 and 610 retain their respective callouts and a description of these common components will not be repeated here for the sake of clarity and conciseness.

Figure 7:
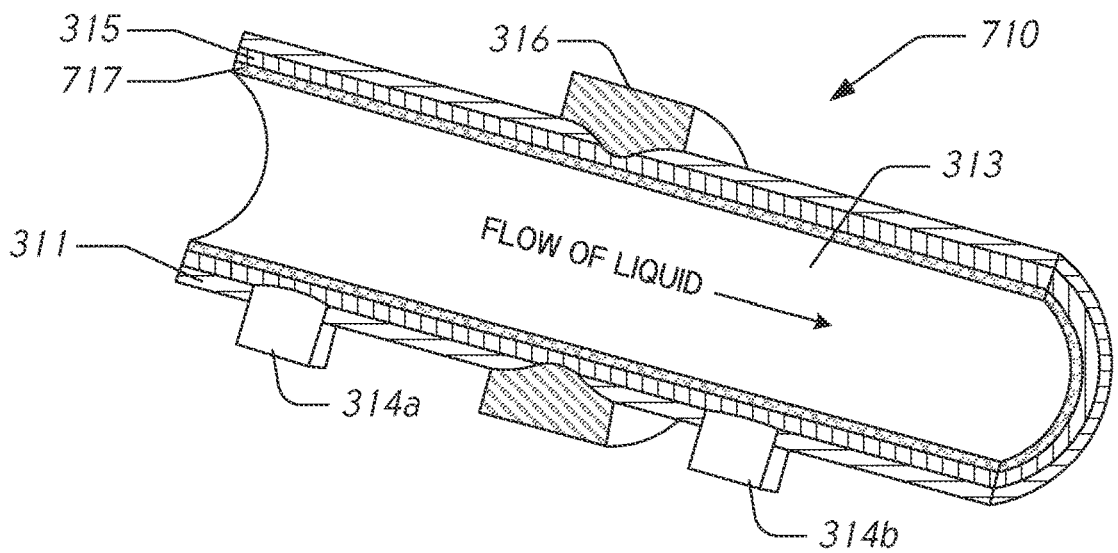
FIG. 7 illustrates an embodiment of the flow probe of FIG. 6.

FIG. 7 illustrates another example flow probe 710, where the flow probe 710 is an embodiment of the flow probe 610 described herein with reference to FIG. 6. The flow probe 710 is also similar to the flow probe 310 described herein with reference to FIG. 3 with a difference being the inclusion of an inner layer 717 that prevents or inhibits physical contact while allowing thermal contact between a liquid flowing through the conduit 313 and the film 315. For example, the wall 311 can be formed with a cavity that allows the thermally-conducting material 315 to be deposited therein so that a portion of the 311 wall forms the inner layer 717 that is between the liquid and the thermally-conducting material 315. As another example, a conformal coating of waterproof, biocompatible material can be the inner layer 717. Elements that are common between the flow probes 310 and 710 retain their respective callouts and a description of these common components will not be repeated here for the sake of clarity and conciseness.

Example Flow Probe System

Figure 8:
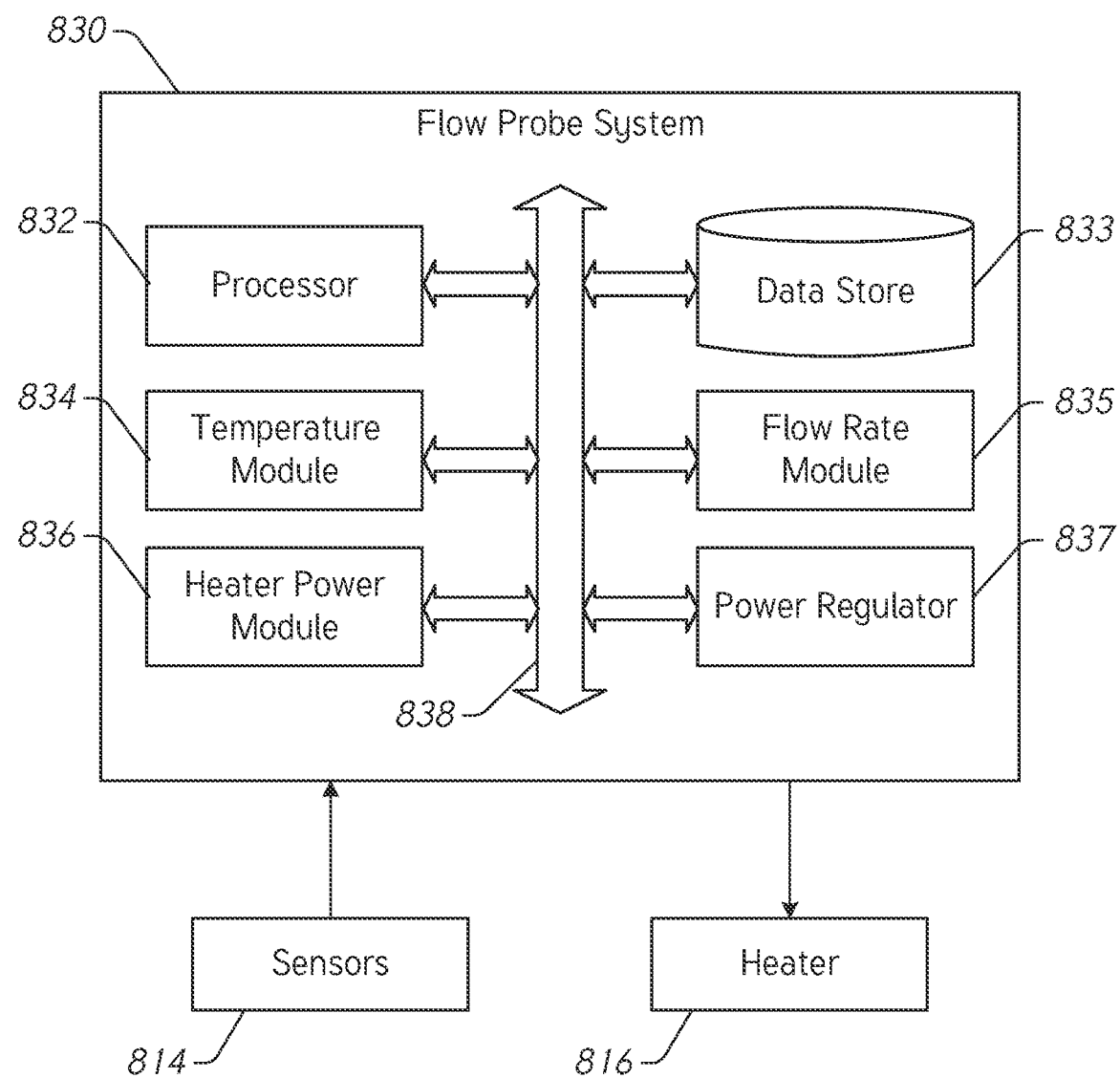
FIG. 8 illustrates an example of a flow probe system that is configured to determine flow rates of a liquid flowing through a conduit of an associated flow probe.

FIG. 8 illustrates an example of a flow probe system 830 that is configured to determine flow rates of a liquid flowing through a conduit of an associated flow probe. The associated flow probe can be any of the flow probes described herein with reference to FIGS. 1-7. The flow probe system 830 can be integrated as a part of any of those flow probes, such as part of the flow probe electronics 218 described herein with reference to FIG. 2. The flow probe system 830 can employ any method described herein for determining a liquid flow rate, such as the example method 900 described herein with reference to FIG. 9.

The flow probe system 830 receives measurement data from temperature sensors 814. The temperature sensors 814 can be any of the temperature sensors of the flow probes described herein with reference to FIGS. 1-7. For example, the sensors 814 can include a proximal and a distal temperature sensor (e.g., thermistors) configured to provide upstream and downstream temperature measurements of a thermally-conducting material in thermal contact with the liquid flowing through the flow probe, as described in greater detail herein.

The flow probe system 830 controls an amount of electrical power provided to a heater 816. The heater 816 can be any of the heaters or heating elements described herein. For example, the heater 816 can be a thin-film heater coupled to a thermally-conducting material in thermal contact with the liquid flowing through the flow probe, as described in greater detail herein. When the flow probe system 830 provides electrical power to the heater 816, the heater generates heat that is transferred to the liquid through the thermally-conducting material, thereby raising the temperature of the liquid (or a small band of the liquid in close proximity to the heater 816). This temperature difference is detected and determined by the flow probe system 830 based on the signals indicative of measured temperatures received from the sensors 814.

The flow probe system 830 can include hardware, software, and/or firmware components for communicating with the sensors 814, controlling the heater 816, and determining a liquid flow rate through an associated flow probe. The flow probe system 830 can include one or more processors 832, a data store 833, a temperature module 834, a flow rate module 835, a heater power module 836, and a power regulator 837. Components of the flow probe system 830 can communicate with one another, with external systems, and with other components of a subject monitoring system or a network using communication bus 838.

The flow probe system 830 includes the temperature module 834. The temperature module 834 is configured to receive signals from the sensors 814, the signals being indicative of measured temperatures. The temperature module 834 converts these signals to temperatures and/or to numbers or signals suitable for further processing in the flow probe system 830 to calculate flow rate and/or to use in determining an output power for the heater 816. The temperature module 834 can be configured to determine an upstream or proximal temperature of the thermally-conductive material upstream of the heater 816. The temperature module 834 can also be configured to determine a downstream or distal temperature of the thermally-conductive material at the heater 816 or downstream of the heater 816. The temperature module 834 can also be configured to determine the temperature difference between the proximal and distal sensors 814. The determined temperatures and/or temperature differences can be sent to the flow rate module 835 for determining the flow rate and/or to the heater power module 836 for determining the power to be provided to the heater 816, as described in greater detail herein.

The flow probe system 830 includes the heater power module 836. The heater power module 836 is configured to determine a power to deliver to the heater 816 to maintain a targeted temperature differential as calculated by the temperature module 834. In response to determining that the temperature differential is too large (e.g., greater than a targeted temperature differential), the heater power module 836 can reduce the amount of power for delivery to the heater 816. Similarly, in response to determining that the temperature differential is too small (e.g., less than a targeted temperature differential), the heater power module 836 can increase the amount of power for delivery to the heater 816. The heater power module 836 is configured to continuously, intermittently, or periodically determine an updated heater power for delivery to the heater 816 based on updated measurements or calculations received from the temperature module 834. The heater power module 836 can dynamically adjust the heater power based on a control scheme, such as a PID control scheme. Control parameters (e.g., PID parameters) can be stored in the data store 833 for use by the heater power module 836. In some embodiments, the heater power module 836 can update control parameters based on feedback from the temperature module 834, the flow rate module 835, the power regulator 837, and/or user input. The heater power module 836 can communicate the output power to the power regulator 837 and to the flow rate module 835.

The flow probe system 830 includes the power regulator 837. The power regulator 837 receives a power setting from the heater power module 836, regulates a power received from a power supply, and delivers the regulated power to the heater 816. The power supply can be internal to the flow probe system 830, such as a battery, or it can be external to the flow probe system 830 where an electrical cable enables transfer of power, such as from a wall outlet, a patient monitor, or other external system or device. As described herein, the power regulator 837 can be a precision power regulator to provide targeted incremental and decremental changes to the heater power to achieve a targeted temperature profile, as described herein. For example, the power regulator 837 can control a 14-bit DAC that can be used to provide sub-millivolt resolution over a range of about 15 V. As another example, the power regulator can have a relatively high temporal resolution or it can include a DAC in conjunction with pulse-width-modulation (PWM) to emulate a relatively high temporal resolution where the temporal resolution of the power regulator is configured to provide a targeted response time of less than about 15 s, less than about 10 s, less than about 7 s, less than about 5 s, less than about 2 s, or less than about 1 s.

The flow probe system 830 includes the flow rate module 835. The flow rate module 835 is configured to receive the temperature calculations from the temperature module 834 and the heater power from the heater power module 836 and to determine a liquid flow rate based on these values. The flow rate module 835 is configured to determine flow rate by associating the power supplied to the heater 816 to a flow rate based on a targeted temperature differential. In some embodiments, the flow rate module 835 is configured to compare the measured temperature differential to the targeted temperature differential. In response to determining that the measured differential is outside of an acceptable threshold range of the targeted differential, the flow rate module 835 can eschew calculation of the liquid flow rate and send an indication to the heater power module 836 to adjust the heater power based on the comparison of the measured and target temperature differentials. In some embodiments, the flow rate module 835 is configured to determine a liquid flow rate based at least in part on a measured temperature differential and a supplied heater power, regardless if it is within a threshold range of a targeted temperature differential. This measurement can be reported with an associated warning or information indicating it is based on a temperature differential that is outside the targeted range.

In some embodiments, the flow rate module 835 accesses a lookup table in the data store 833 that associates temperature differentials and heater power to liquid flow rates. The lookup table can be generated at a time when the associated flow probe was calibrated and characterized to accurately associate temperature differential and targeted temperature differentials with liquid flow rates. The lookup table can be generated on-site (e.g., at a hospital, in an operating room, or the like) or at the time of manufacture. The data store 833 can include a library of calibrations associated with different liquids and/or operating conditions. The lookup table can be calibrated for different liquid types (e.g., saline, colloid, crystalloid). This enables a single flow probe to accurately measure flow rates for a variety of IV fluids, for example.

In some embodiments, the flow probe system 830 is in communication with a patient monitor, such as the patient monitor 104 described herein with reference to FIG. 1. In various implementations, user input can be received through the flow probe system 830 (e.g., via the patient monitor or through a user interface associated with the flow probe system 830). The user input can be used to inform the flow probe system 830 the type of liquid being used to ensure an appropriate lookup table is used. The user input can also be used to respond to prompts from the flow probe system 830 and/or to control operating parameters of the flow probe system 830.

In some embodiments, an algorithm can be implemented to detect a major discontinuity in the baseline flow rate (e.g., a slow, steady flow) and prompt a clinician to confirm that fluid type has not changed. The prompt can be provided over the patient monitor, for example. Similarly, the algorithm can be configured to detect a break in the flow of liquids (e.g., no flow) for a period of time, which may indicate that an IV bag is being changed. In such instances, the flow probe system 830 can request confirmation that the fluid type has not been changed. The prompt can be provided over the patient monitor, for example. In some implementations, a lack of response or if no response is received within a designated time window, the flow probe system 830 can resume operation assuming no change in liquid type has occurred. In certain embodiments, the algorithm can be used to determine the fluid type. For example, after a no-flow condition has been determined, the algorithm can be used to calculate thermal dissipation properties after flow begins again and can determine the type of liquid based on these calculated properties. This determination can then be used to select an appropriate calibration lookup table. The algorithm can be implemented onboard the flow probe system 830, it can be implemented on the patient monitor, or it can be implemented on a combination of the flow probe system 830 and the patient monitor.

The flow probe system 830 includes one or more processors 832 that are configured to control operation of the modules 834, 835, 836, the power regulator 837, and the data store 833. The one or more processors 832 implement and utilize the software modules, hardware components, and/or firmware elements configured to determine liquid flow rates in an associated flow probe. The one or more processors 832 can include any suitable computer processors, application-specific integrated circuits (ASICs), field programmable gate array (FPGAs), or other suitable microprocessors. The one or more processors 832 can include other computing components configured to interface with the various modules and data stores of the flow probe system 830.

The flow probe system 830 includes the data store 833 configured to store configuration data, calibration data, device data, measurement data, lookup tables (e.g., heater power to flow rate, temperature difference to flow rate, heater power and temperature difference to flow rate, etc.) databases, data tables, algorithms, executable instructions (e.g., instructions for the one or more processors 832), and the like. The data store 833 can be any suitable data storage device or combination of devices that include, for example and without limitation, random access memory, read-only memory, solid-state disks, hard drives, flash drives, bubble memory, and the like.

In some embodiments, the hardware components of the flow probe system 830 can be discrete components or large-scale electronics. The components can be selected so that flow probe system 830 survives electron-beam (or e-beam) sterilization (e.g., remains operable after the sterilization process).

Example Flow Rate Measurement Methods

Figure 9:
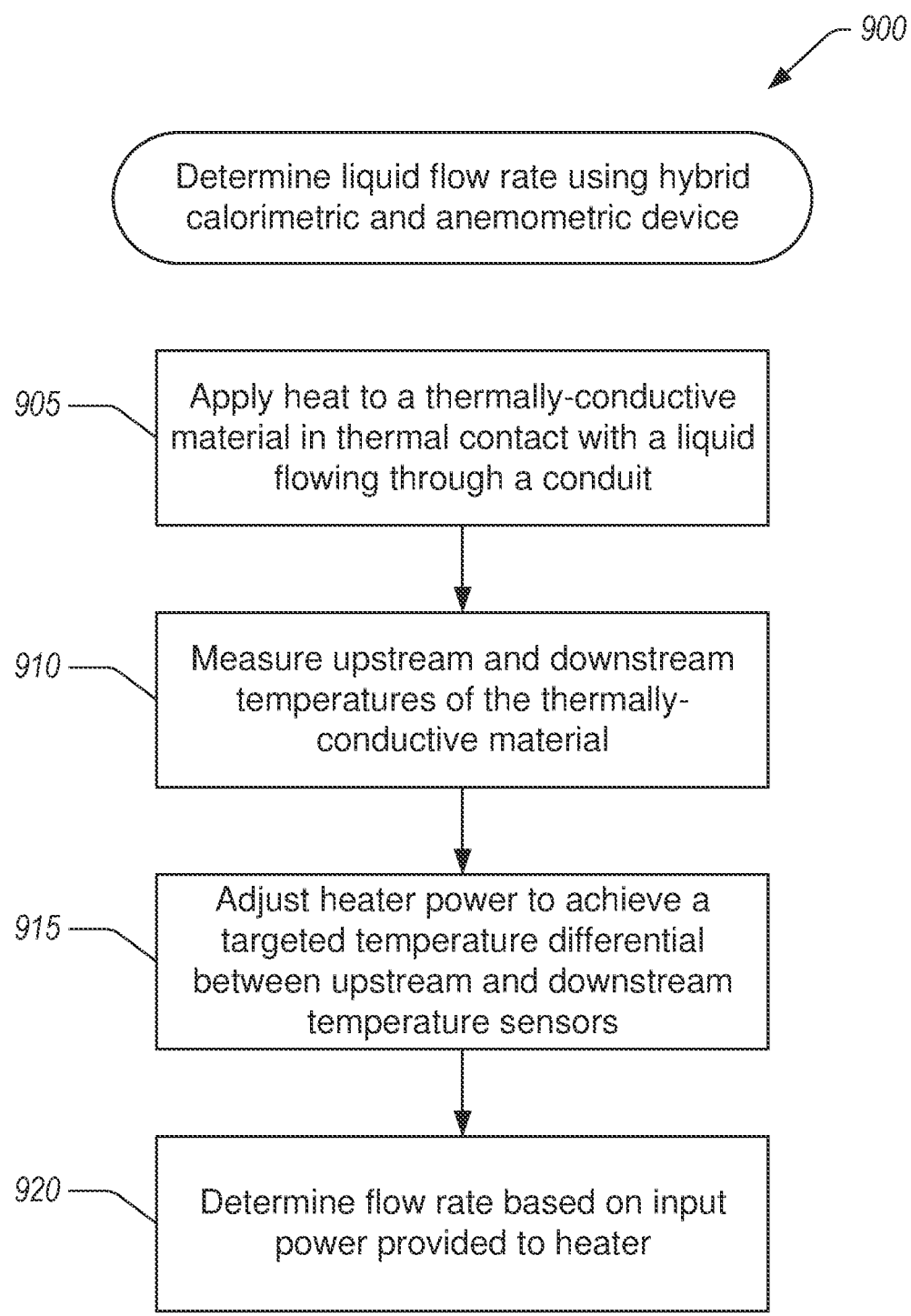
FIG. 9 illustrates a flow chart of an example method for determining liquid flow rates using a hybrid calorimetric and anemometric device.

FIG. 9 illustrates a flow chart of an example method 900 for determining liquid flow rates using a hybrid calorimetric and anemometric device. The method 900 can be performed by any of the flow probes described herein with reference to FIGS. 1-7 and/or the flow probe system described herein with reference to FIG. 8. For ease of description, the method 900 will be described as being performed by a flow probe. However, this should not be understood to limit the scope of the disclosure. Rather, any step or portion of the method 900 can be performed by any component or combination of components of the systems described herein.

In block 905, the flow probe applies heat to a thermally-conductive material in thermal contact with a liquid flowing through a conduit. The flow probe provides power to a heater that is in thermal contact with the thermally-conductive material. The heat generated by the heater is transferred to the liquid through the thermally-conductive material.

In block 910, the flow probe measures an upstream and a downstream temperature of the thermally-conductive material. The upstream temperature measurement is indicative of the temperature of the liquid upstream of the heater or upstream of where heat is being applied to the thermally-conductive material. The downstream temperature measurement is indicative of the temperature of the liquid downstream of the heater or downstream of where heat is being applied to the thermally-conductive material. The upstream and downstream temperatures can be measured by any suitable temperature sensor, as described herein.

In block 915, the flow probe adjusts power to the heater to achieve a targeted temperature differential between the upstream and downstream temperature sensors. The targeted temperature differential can be determined prior to operating the flow probe. In some embodiments, the targeted temperature differential can be adjusted by a user or by the flow probe itself based on temperature measurements and/or heater power calculations.

In block 920, the flow probe determines a flow rate of the liquid based at least in part on the measured temperature differential and the power provided to the heater. Where the targeted temperature differential is achieved, the flow probe can determine the flow rate based on the power provided to the heater.

Additional Embodiments and Terminology

The terms "subject" and "patient" are used interchangeably herein and relate to mammals, inclusive of warm-blooded animals (domesticated and non-domesticated animals), and humans. The terms "clinician" and "healthcare provider" are used interchangeably herein.

The term "sensor" as used herein relates to a device, component, or region of a device capable of detecting and/or quantifying and/or qualifying a physiological parameter of a subject. The phrase "system" as used herein relates to a device, or combination of devices operating at least in part in a cooperative manner, that is inclusive of the "sensor." Sensors generally include those that continually measure the physiological parameter without user initiation and/or interaction ("continuous sensing device" or "continuous sensor"). Continuous sensors include devices and monitoring processes wherein data gaps can and/or do exist, for example, when a continuous pressure sensor is temporarily not providing data, monitoring, or detecting. Sensors also generally include those that intermittently measure the physiological parameter with or without user initiation and/or interaction ("intermittent sensing device" or "intermittent sensor"). In some embodiments, sensors, continuous sensing devices, and/or intermittent sensing devices relate to devices, components, or regions of devices capable of detecting and/or quantifying and/or qualifying a physiological hemodynamic parameter of a subject.

The phrases "physiological data," "physiological parameter," and/or "hemodynamic parameter" include without limitation, parameters directly or indirectly related to providing or calculating blood pressure (BP), stroke volume (SV), cardiac output (CO), end-diastolic volume, ejection fraction, stroke volume variation (SVV), pulse pressure variation (PPV), systolic pressure variations (SPV), extravascular lung water index (ELWI), pulmonary vascular permeability index (PVPI), global end-diastolic index (GEDI), global ejection fraction (GEF), systolic volume index (SVI), arterial blood pressure (ABP), cardiac index (CI), systemic vascular resistance index (SVRI), peripheral resistance (PR), central venous saturation (ScvO2), and plethysmographic variability index (PVI). Hemodynamic parameters are inclusive of the absolute value of such parameters, a percentage change or variation in the parameters since an event was recorded, and an absolute percentage change within a previous time segment.

The phrases "electronic connection," "electrical connection," "electrical contact" as used herein relate to any connection between two electrical conductors known to those in the art. In some embodiments, electrodes are in electrical connection with (e.g., electrically connected to) the electronic circuitry of a device.

The term and phrase "electronics" and "system electronics" as used herein relate to electronics operatively coupled to the sensor and configured to measure, process, receive, and/or transmit data associated with a sensor, and/or electronics configured to communicate with a monitor or a data acquisition device.

The phrases "operatively connected," "operatively linked," "operably connected," and "operably linked" as used herein relate to one or more components linked to one or more other components, such that a function is enabled. The terms can refer to a mechanical connection, an electrical connection, or any connection that allows transmission of signals between the components. For example, one or more transducers can be used to detect pressure and to convert that information into a signal; the signal can then be transmitted to a circuit. In such an example, the transducer is "operably linked" to the electronic circuitry. The terms "operatively connected," "operatively linked," "operably connected," and "operably linked" include wired and wireless connections.

The term and phrase "controller," "processor" or "processing module," as used herein relates to components and the like designed to perform arithmetic or logic operations using logic circuitry that responds to and processes basic instructions, for example, instructions that drive a computer and/or perform calculations of numbers or their representation (e.g., binary numbers).

The terms "substantial" and "substantially" as used herein relate to a sufficient amount that provides a desired function.

For example, an amount greater than 50 percent, an amount greater than 60 percent, an amount greater than 70 percent, an amount greater than 80 percent, or an amount greater than 90 percent.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described herein. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments. The terms "comprising," "including," "having," "characterized by," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

Reference throughout this specification to "certain embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional subcomponents to be performed separately. In some instances, the order of the steps and/or phases can be rearranged, and certain steps and/or phases may be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general-purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any computing device described herein. In such distributed embodiments, the functions of the one computing device are distributed (e.g., over a network) such that some functions are performed on each of the distributed computing devices.

Some embodiments may be described with reference to equations, algorithms, and/or flowchart illustrations. These methods may be implemented using computer program instructions executable on one or more computers. These methods may also be implemented as computer program products either separately, or as a component of an apparatus or system. In this regard, each equation, algorithm, block, or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation(s), algorithm(s), and/or block(s) of the flowchart(s).

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips and/or magnetic disks, into a different state.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list. The word "exemplary" is used exclusively herein to mean "serving as an example, instance, or illustration." Any implementation described herein as "exemplary" is not necessarily to be construed as preferred or advantageous over other implementations.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A flow probe comprising:
    a housing with walls forming a conduit to allow a liquid to flow therethrough, the housing further forming a cavity such that the walls form an inner layer between the conduit and the cavity;
    a thermally-conductive material deposited within the cavity formed by the housing such that a flow of liquid is between opposite portions of the thermally-conductive material and such that the inner layer is between a liquid flowing in the conduit and the thermally-conductive material such that the inner layer prohibits physical contact between the liquid flowing through the conduit and the thermally-conductive material;
    a heating element coupled to an outer portion of the walls with a portion of the heating element penetrating through the walls to be in thermal contact with the thermally-conductive material so that the heating element is not exposed to the conduit;
    a proximal temperature sensor upstream of the heating element, the proximal temperature sensor coupled to an outer portion of the walls with a portion of the proximal temperature sensor penetrating through the walls to be in thermal contact with the thermally-conductive material so that the proximal temperature sensor is not exposed to the conduit;
    a distal temperature sensor downstream of the heating element, the distal temperature sensor coupled to an outer portion of the walls with a portion of the distal temperature sensor penetrating through the walls to be in thermal contact with the thermally-conductive material so that the distal temperature sensor is not exposed to the conduit; and a controller in communication with the heating element, the proximal temperature sensor, and the distal temperature sensor, the controller configured to:

control the heating element to apply heat to the thermally-conductive material;

determine an upstream temperature based at least in part on signals received from the proximal temperature sensor;

determine a downstream temperature based at least in part on signals received from the distal temperature sensor;

adjust a heater power provided to the heating element based at least in part on a determined temperature differential between the downstream temperature and the upstream temperature, the adjustment to the heater power being configured to achieve an adjustable targeted temperature differential; and determine, when the targeted temperature differential has been achieved, a liquid flow rate using the adjusted heater power provided to the heating element, and the achieved targeted temperature differential between the downstream temperature and the upstream temperature.

2. The flow probe of claim 1 further comprising system electronics in communication with the proximal and distal temperature sensors, the controller, and the heating element.

3. The flow probe of claim 2 wherein the system electronics includes electronics configured to withstand electron beam or gamma-ray sterilization.

4. The flow probe of claim 2 wherein the system electronics are not semi-conductor based.

5. The flow probe of claim 4 wherein the system electronics include discrete electronic components and MEMS-based fabrication techniques.

6. The flow probe of claim 1 wherein the flow probe is shuntless.

7. The flow probe of claim 1 wherein the flow probe includes luer lock connectors on a proximal end and a distal end of the housing.

8. The flow probe of claim 1 wherein the flow probe is configured for use in an intravenous line.

9. The flow probe of claim 1 wherein the proximal temperature sensor is positioned between 25 mm and 50 mm from a proximal end of the conduit.

10. The flow probe of claim 1 wherein the distal temperature sensor is positioned less than or equal to 5 mm from a distal end of the heating element.

11. The flow probe of claim 1 wherein the proximal temperature sensor is a thin-film thermocouple.

12. The flow probe of claim 1 wherein the proximal temperature sensor is a thermistor.

13. The flow probe of claim 1 wherein the heating element is a thin-film heating element.

14. The flow probe of claim 1 wherein the controller implements a proportional-integral-derivative control scheme to control the heating element.

15. The flow probe of claim 1 wherein the flow probe is configured for use with liquids in a temperature range greater than or equal to 5° C. and less than or equal to 50° C.

16. The flow probe of claim 1 wherein the flow probe is configured for use with liquids with flow rates in a range greater than or equal to 0 mL/min and less than or equal to 180 mL/min.

17. The flow probe of claim 1 wherein the flow probe is configured to be responsive to changes in flow rate in less than 1 second.

18. The flow probe of claim 1 wherein the distal temperature sensor is integrated with the heating element.

19. The flow probe of claim 1 wherein the controller determines liquid flow rate using a lookup table that associates heater power to flow rate.

20. The flow probe of claim 1, wherein the inner layer is configured to be biocompatible with human fluid and waterproof.

21. A method for determining liquid flow rate using a flow probe device, the method comprising:

directing a liquid through a conduit formed by walls of a housing of the flow probe device, the housing further forming a cavity such that the walls form an inner layer between the conduit and the cavity;

applying heat to a thermally-conductive material deposited within the cavity formed by the housing such that a flow of liquid is between opposite portions of the thermally-conductive material and such that the inner layer is between a liquid flowing in the conduit and the thermally-conductive material such that the inner layer prohibits physical contact between the liquid flowing through the conduit and the thermally-conductive material;

measuring a temperature upstream of a heating element of the flow probe device using a proximal temperature sensor;

measuring a temperature downstream of the heating element using a distal temperature sensor;

adjusting heater power provided to the heating element to achieve an adjustable targeted temperature difference between the upstream temperature and the downstream temperature; and determining, when the targeted temperature difference has been achieved, a flow rate based on using the adjusted heater power provided to the heating element, and the achieved temperature difference between the downstream temperature and the upstream temperature, wherein each of the heating element, the proximal temperature sensor, and the distal temperature sensor is coupled to an outer portion of the walls with a portion of each of the heating element, the proximal temperature sensor, and the distal temperature sensor penetrating through the walls and is separated from the liquid flowing through the conduit by the thermally-conductive material.

22. The method of claim 21 wherein determining the flow rate is also based on the difference between the measured upstream temperature and the measured downstream temperature.

23. The method of claim 21 wherein measuring the upstream temperature includes measuring a temperature of the thermally-conductive material.

24. The method of claim 23 wherein measuring the downstream temperature includes measuring a temperature of the thermally-conductive material at the heating element.

25. The method of claim 23 wherein measuring the downstream temperature includes measuring a temperature of the thermally-conductive material less than 5 mm from the heating element.

26. The method of claim 21 wherein applying heat to the thermally-conductive material includes heating the heating element that is in thermal contact with the thermally-conductive material.

27. The method of claim 21 wherein adjusting power includes using a proportional-integral-derivative control scheme to control the heating element.

28. The method of claim 21 further comprising adjusting the targeted difference between the upstream temperature and the downstream temperature.

29. The method of claim 21 wherein determining the flow rate is also based on the targeted difference between the upstream temperature and the downstream temperature.

30. The method of claim 21 wherein determining the flow rate accounts for non-linear cooling effects.

\* \* \* \* \*